United States Patent [19]
Caillouette

[11] Patent Number: 5,735,801
[45] Date of Patent: Apr. 7, 1998

[54] ESTROGEN OR ESTRADIOL NEED DETERMINATION BY VAGINAL ACIDITY DETERMINATION

[76] Inventor: James C. Caillouette, 685 Oak Knoll Cir., Pasadena, Calif. 91106

[21] Appl. No.: 699,251

[22] Filed: Aug. 19, 1996

Related U.S. Application Data

[63] Continuation-in-part of Ser. No. 570,534, Dec. 11, 1995, which is a continuation-in-part of Ser. No. 537,379, Oct. 27, 1995, Pat. No. 5,577,512, which is a continuation-in-part of Ser. No. 376,830, Jan. 23, 1995, Pat. No. 5,664,579, which is a continuation-in-part of Ser. No. 295,399, Aug. 25, 1994, Pat. No. 5,425,377.

[51] Int. Cl.⁶ .................................................. A61B 5/00
[52] U.S. Cl. .................................................. 600/572; 600/584
[58] Field of Search ................................. 128/749, 759, 128/760, 771

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 4,820,259 | 4/1989 | Stevens . |
| 4,862,899 | 9/1989 | Bucaro . |
| 5,063,930 | 11/1991 | Nucci . |
| 5,147,288 | 9/1992 | Schiavo . |
| 5,527,534 | 6/1996 | Myhling ............... 424/430 |

OTHER PUBLICATIONS

Peter Smith, Dept. of Obstetrics & Gynecology, University Hospital, S–751 85 Uppsala, Sweden "Estrogens and the Urogenital Tract" 1993.

Gloria Bachmann, Maturitas 22 Suppl. (1995) S21–S29 "The Estradiol Vaginal Ring—A Study of Existing Clinical Data" 1995.

"Vulvovaginitis", vol. 1, Chapter 37, Ronald M. Meltzer 1994.

"Urinary Incontinence and Related Urogenital Symptoms in Elderly Women", Ulla Molander, Scandinavian Association of Obstetricians and Gynecologists, Supplement 158, vol. 72, 1993.

"Estrogen Deprivation and Vaginal Function in Postmenopausal Women", James P. Semmens, MD, Gorm Wagner, MD 1982.

*Primary Examiner*—Max Hindenburg
*Attorney, Agent, or Firm*—William W. Haefliger

[57] ABSTRACT

In the method of determining need for human estrogen replacement therapy or estrogen or estradiol dose change, the steps include determining local acidity proximate a moist wall surface of the vagina, as differing from desired threshold level (pH 4.5), and administering sufficient estrogen or estradiol to result in change in acidity toward such level.

24 Claims, 5 Drawing Sheets

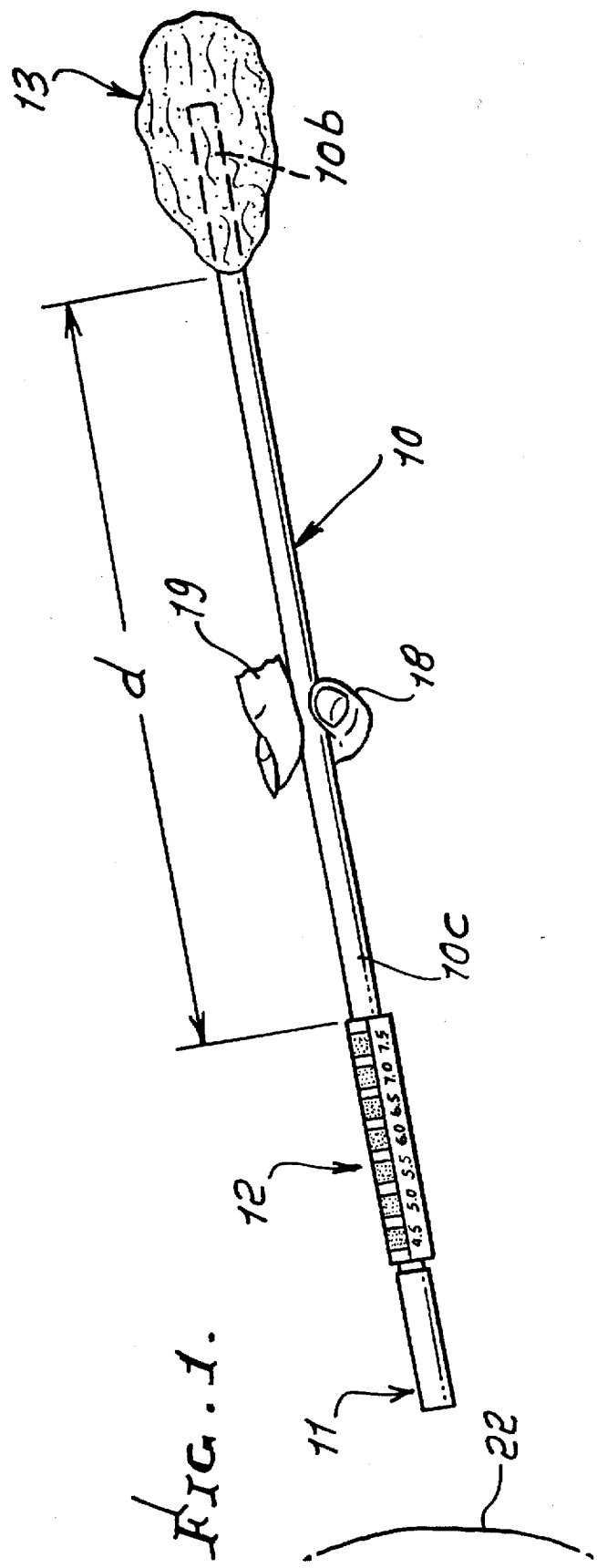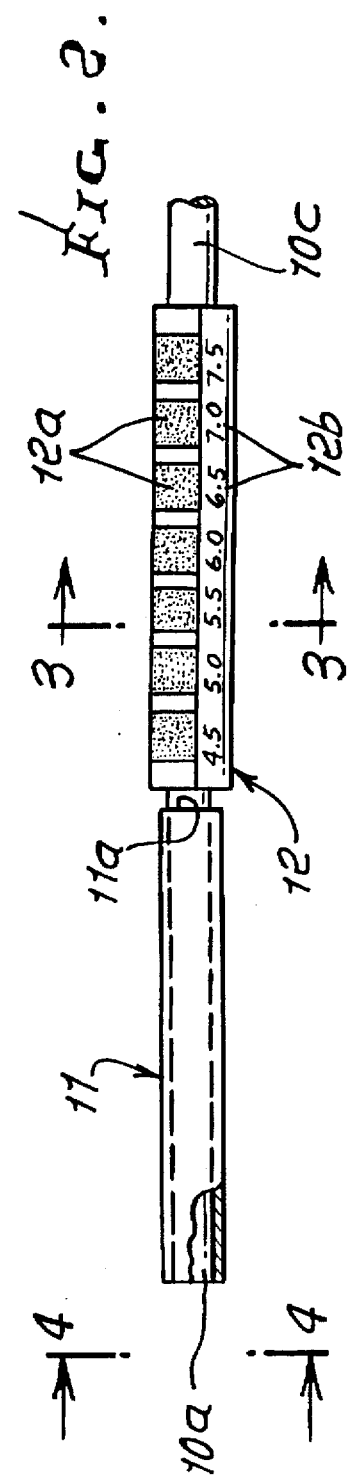

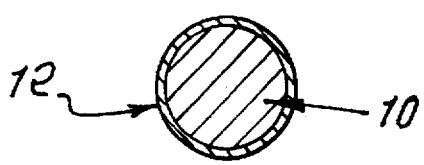
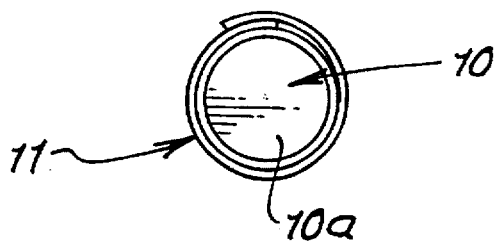
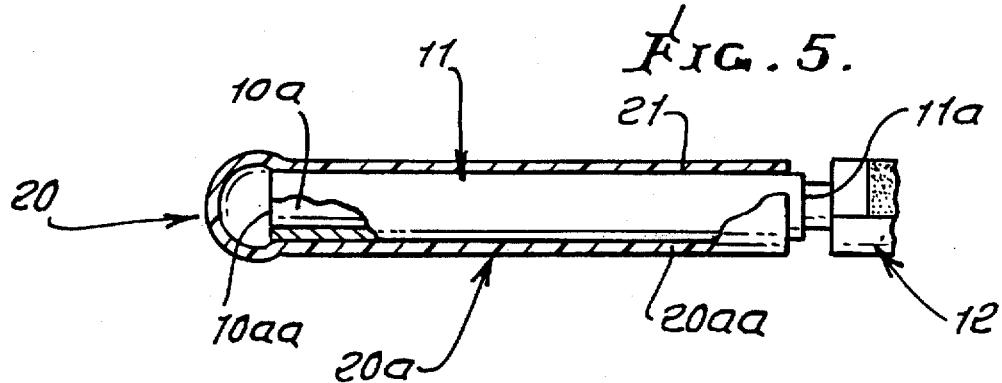
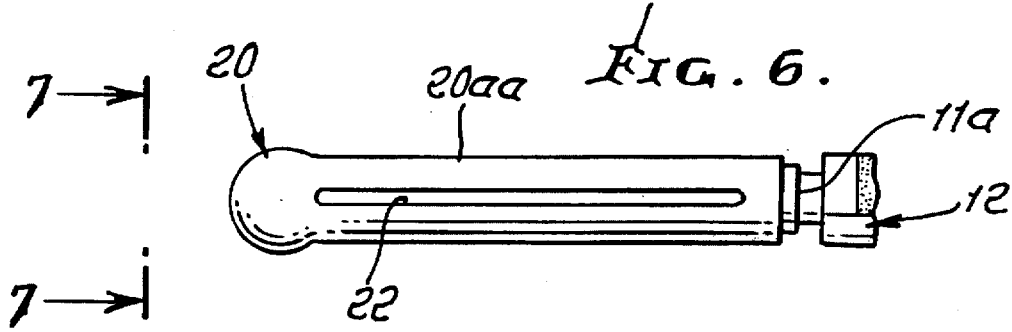
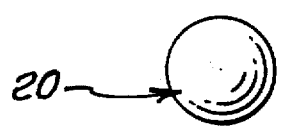

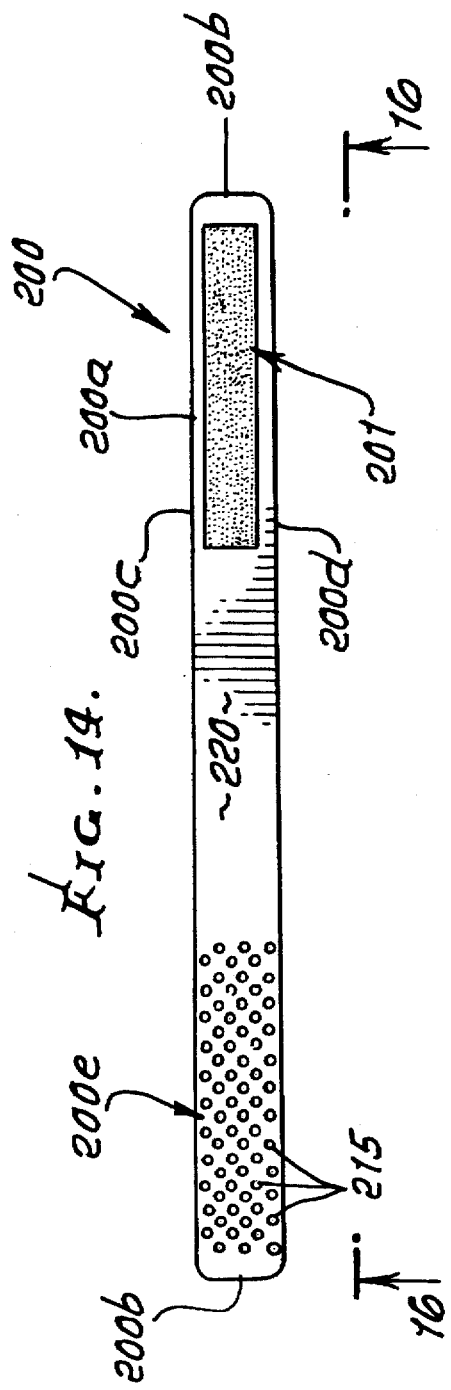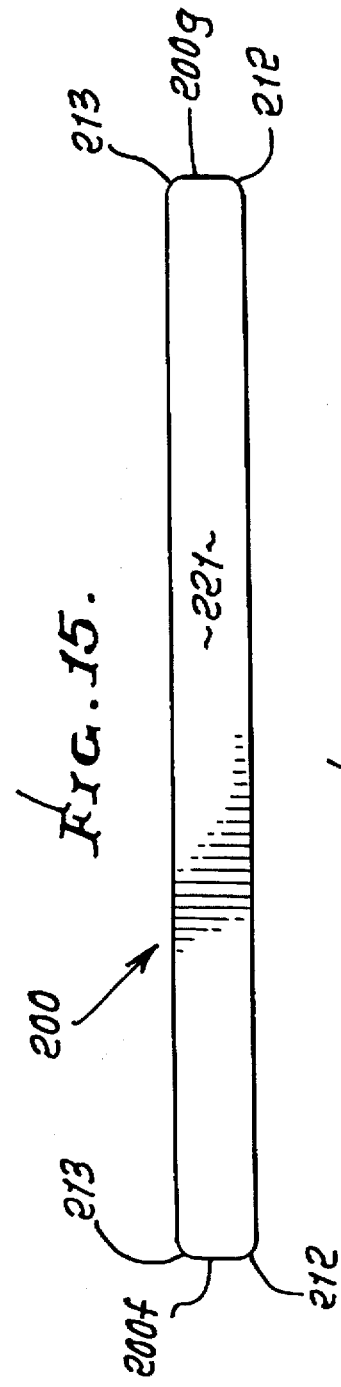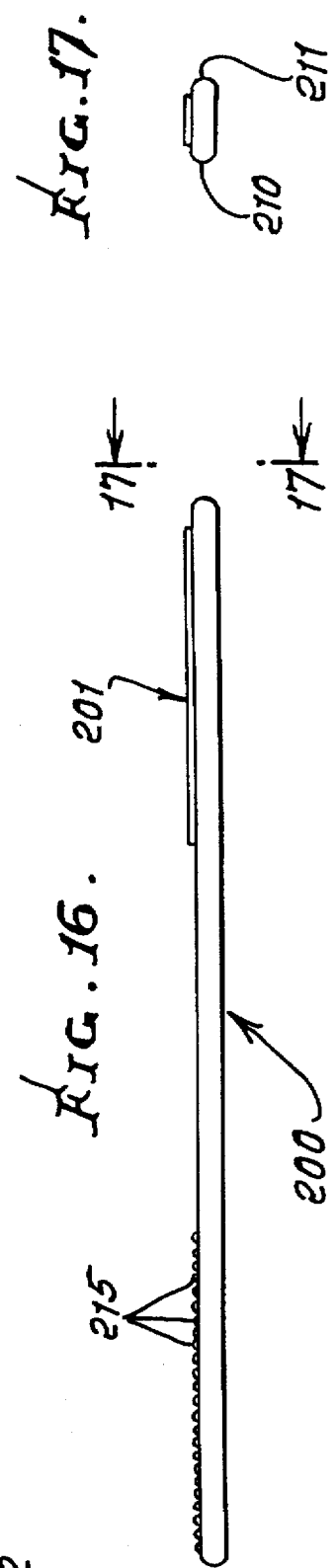

5,735,801

1

ESTROGEN OR ESTRADIOL NEED DETERMINATION BY VAGINAL ACIDITY DETERMINATION

BACKGROUND OF THE INVENTION

This application is a continuation-in-part of prior U.S. application Ser. No. 08/570,534 filed Dec. 11, 1995, now pending, which is a continuation-in-part of prior U.S. application Ser. No. 08/537,379 filed Oct. 27, 1995, now U.S. Pat. No. 5,577,512, which is a continuation-in-part of prior U.S. application Ser. No. 08/376,830 filed Jan. 23, 1995, now U.S. Pat. No. 5,644,579, which is a continuation-in-part of prior U.S. application Ser. No. 08/295,399 filed Aug. 25, 1994, now U.S. Pat. No. 5,425,377.

This invention relates generally to factors involved in determining estrogen or estradiol administration to human females, and more particularly to a simple and effective method and means to effect such determination such as need for beginning estrogen replacement therapy or changes in dosage of estrogen or estradiol.

There is need for improvements in methods to determine whether or not a human female should be administered estrogen or estradiol or needs a higher or lower dose of estrogen or estradiol. The present invention addresses that need.

SUMMARY OF THE INVENTION

It has been discovered that the acidity (ph) or ph(acidity) level of a moist wall surface of the vagina can be employed in estrogen or estradiol need determination. In accordance with the invention, the method of determining need for estrogen or estradiol increase or decrease includes the steps:

a) determining local acidity proximate a moist wall surface of the vagina, as differing from desired threshold level, and in the substantial absence of bacterial vaginosis or vaginitis, or other contaminants such as medications, blood, semen, b) and administering sufficient estrogen or estradiol or estrogenic substance to result in change in acidity toward such level or a pH of about 4.5 without menopausal signs or symptoms.

Typically, administering of sufficient estrogen or estradiol may be effected on a periodic regular basis, as for example increased or decreased dosage on a daily basis, and in increasing amounts, and said determination of local acidity is repeated, whereby said local acidity is ultimately determined to have reached said desired level.

Yet another object is the carrying out of such determination of local acidity as by employing an acidity indicator, for contacting the wall surface of the vagina. Such an indicator may desirably include one of the following:

i) NITRAZINE® paper ii) phenaphthazine on a carrier iii) a material or materials exhibiting different colorations or other indicators as a function of pH level.

A strip of material may be used to carry the indicator, and such a strip may be employed in contacting the vaginal wall. One method of use is to provide the strip of material on an applicator, an example being a carrier stick which is easily manipulable.

A further object is to provide a pH level indicator comprising a material or materials exhibiting colorations corresponding to pH levels of moisture of the wall surface of the vagina, said colorations being different for different pH levels. The desired threshold level of acidity is approximately 4.2–4.5.

2

Yet another object is to provide a method that includes the steps:

a) providing an acidity sensing means on a carrier, b) providing a protective porous layer adjacent said sensing means, c) manipulating the carrier proximate vaginal moisture, and including allowing vaginal moisture to penetrate said porous layer for contact with said sensing means, d) and detecting a vaginal moisture produced change in said sensing means for determining need for beginning estrogen replacement therapy or a change in estrogen or estradiol dose to be administered to a human female.

An additional object is to measure vaginal pH for screening purposes, a vaginal pH level of 4.5 being consistent with a physiologic serum estradiol and the absence of bacterial vaginosis. An elevated vaginal pH in the 5.0–6.5 range suggests a diagnosis of either bacterial vaginosis or decreased serum estradiol. In patients with an elevated pH, vaginal culture should establish the diagnosis. In the absence of vaginosis, a vaginal pH of 6.5–7.5 is strongly suggestive of a low serum estradiol or menopause. Titration of estradiol level by vaginal pH during estrogen replacement therapy is then carried out.

These and other objects and advantages of the invention, as well as the details of an illustrative embodiment, will be more fully understood from the following specification and drawings, in which:

DRAWING DESCRIPTION

FIG. 1 is a side elevational view of stick apparatus incorporating the invention;

FIG. 2 is an enlarged side view of one end portion of the FIG. 1 stick apparatus;

FIG. 3 is an enlarged section taken on lines 3—3 of FIG. 2;

FIG. 4 is an enlarged end view taken on lines 4—4 of FIG. 2;

FIG. 5 is an elevation, partly in section, showing a modification;

FIG. 6 is a side elevation of the FIG. 5 modification;

FIG. 7 is an end view taken on lines 7—7 of FIG. 6;

FIG. 14 is a plan view of the top side of a modified stick apparatus;

FIG. 15 is a plan view of the bottom side of the FIG. 14 stick apparatus;

FIG. 16 is an edge view taken on lines 16—16 of FIG. 14; and

FIG. 17 is an end view taken on lines 17—17 of FIG. 16.

DETAILED DESCRIPTION

As referred to, the method of the invention concerns determining need for estrogen replacement therapy or estrogen or estradiol dose change, through vaginal wall pH determination. Typical steps include:

a) determining local acidity proximate a moist wall surface of the vagina, as differing from desired threshold level, as in the substantial absence of bacterial vaginosis, or other contaminants such as medication, blood, semen, b) and administering sufficient estrogen or estradiol to result in change in said acidity toward said level.

A more complete method includes:

a) first determining local acidity proximate a moist wall surface of the vagina, said determining employed as an indicator of the presence or absence of bacterial vaginosis, b) and, after a vaginosis condition has been treated and eliminated, then again determining local acidity proximate a moist wall surface of the vagina, as differing from desired threshold level, c) and administering sufficient estrogen or estradiol to result in change in said acidity toward said threshold level.

Figure 13:
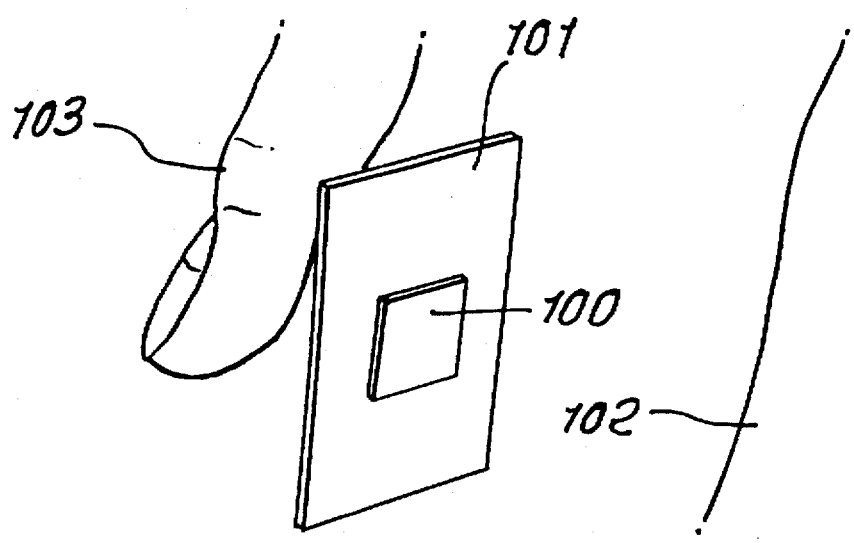
FIG. 13 is a perspective view showing pH indicator manipulation manually.

A pH indicator 100, as seen in FIG. 13 may be employed, and that indicator may be located on a carrier strip 101, which is easily manipulable into contact with the vaginal wall, shown at 102, the user's finger shown at 103 to urge the tissue strip toward the wall surface. Such an indicator may take the form of one of the following, although other indicators are usable.

i) NITRAZINE® paper ii) phenaphthazine on a carrier iii) a material or materials exhibiting different colorations or other indicators as a function of pH level.

The indicator may desirably exhibit different colorations or changes corresponding to different pH levels, of moisture at the vaginal wall, and from which the observed coloration or changes may be used to indicate need for greater or lesser estrogen or estradiol dosage, as on a daily or other periodic basis. In the case of NITRAZINE® paper (phenaphtazine), the correlation of pH to color is as follows:

| pH | Color |
| --- | --- |
| 4.5 | golden yellow |
| 5.0 | beige |
| 5.5 | light olive |
| 6.0 | dark olive |
| 6.5 | olive blue |
| 7.0 | purple blue |
| 7.5 | dark blue |

In a typical example, if the user detected or determined an indicator color of dark olive, it would be determined that an estrogen or estradiol increase above the existing daily level of use would be recommended, in order to diminish pH level to 4.2 to 4.5 within one to two weeks, for example. Testing would be performed on a once a week basis. Thus, if the user had been taking 1 mg. of estrogen or estradiol per day, for example orally, she would be recommended to increase that level to 1.5 mg. per day, the objective being to reduce the pH level to about 4.5 within about 10–21 days. If the tested color were not golden yellow (4.5 pH) after 7–8 days, the dosage might be increased to 2.0 mg. level, per day, until a golden yellow color of the test strip was achieved. Thus, pH determination is indicative of need for change in estrogen or estradiol dosage (up or down).

The indicator may alternatively be employed on a manipulable apparatus, as for example a carrier stick. In FIGS. 1–4, an elongated, narrow carrier stick 10 may consist of wood, plastic, or other material. Provided on the carrier stick are:

a pH indication means, as generally shown at 11, at one end portion 10a of the stick; and a color comparison pH measurement means, as generally indicated at 12, spaced from stick end portion 10a, but close to 11;

As shown, the first means 11 may comprise a pH indication strip, such as a NITRAZINE® (Phenaphthazine) strip, wound about the stick end portion 10a and adhered to same as by an adhesive. NITRAZINE® (Phenaphthazine) strips are products of Bristol-Myers Squibb. The color comparison pH measurement means 12 may comprise a thin paper strip adhered to the stick surface to extend lengthwise of the stick from the edge or end 11a of the first means 11. The second means is shown to have color gradations in a series sequence, as in colored bands 12a, positioned lengthwise of or along the stick. In addition, the paper strip 12 may include pH numerical indicators 12b along side the color gradation bands, to enable:

visual color comparison of the pH indication means 11 (immediately after its exposure to vaginal fluid) with the bands 12a, for visual selection of that band most close in color to the color of the indication means 11;

and immediate visual readout of the pH number adjacent the selected band.

Such readout of pH is then compared with the desired level of about 4.2–4.5 to enable determination of a recommended dosage of estrogen or estradiol, as on a daily basis.

The stick projects freely at 10c away from the first and second means 11 and 12 for manual manipulation (see the grasping finger and thumb 18 and 19), to first obtain pH indication of vaginal wall moisture at one end of the stick, and to enable visual interpretation of that indication by color comparison with the second means, without manual release of the stick. The stick is then disposable, or may be disposed of.

Lengthwise spacing "d" between 12 and stick end 10d is such as to enable free manual manipulation of the stick; and such spacing is typically between 3 and 5 inches, enabling ready finger grasping of the stick and manipulation thereof. In a specific example, "d" is about 4 inches, and the stick diameter or width is about ⅛ inch.

The method of measuring pH of vaginal moisture includes the steps:

a) providing a pH indicator on a carrier stick, b) manipulating the stick to obtain pH indication of vaginal wall moisture at said indicator, c) visually interpreting that indication to determine need for a change in estrogen or estradiol dosage, d) and disposing of the stick, The overall sizes of 11, 12 and 13 are such as to enable ready insertion into the vagina, via stick manipulation at zone 10c.

Referring now to the modification shown in FIGS. 5–7, a smooth surfaced protective tip 20 is provided to face endwise at the end 10aa of the stick end portion 10a. As shown, the tip 20 is endwise convex, as for example bulbous, to provide for or enable comfortable insertion of the stick end portion 10a into the vagina, for pH measurement. The tip 20 may typically be formed integrally with a sleeve 20a assembled over and closely fitting the measurement strip 11, and may be suitably adhered thereto, locally, as at 21. A suitable bonding agent is epoxy. The remainder of the strip 11 is therefore available for pH indication. Alternatively, the sleeve may be attached, as by heat shrinking, or by wedge fit.

A fluid access opening is provided through the wall of the sleeve, whereby vaginal moisture or fluid may access the strip 11 via that opening. See for example elongated slot 22 in the sleeve wall 20aa. The sleeve and tip may consist of transparent, molded, plastic material, to facilitate viewing of a change of color of the strip 11.

Figure 8:
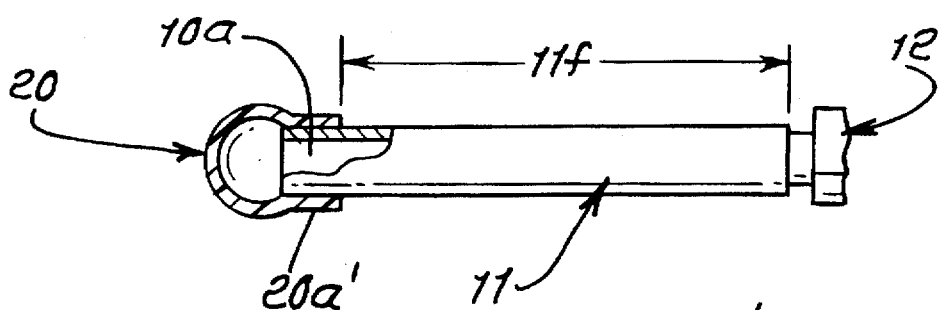
FIG. 8 is an elevation showing a further modification.

In FIG. 8, the sleeve 20a is shortened and attached at sleeve end 20a' into flush, or near flush, relation with the surface of the strip, at a locus on stick end portion 10a. This leaves the remaining length 11f of the strip openly exposed for moisture contact.

Figure 9:
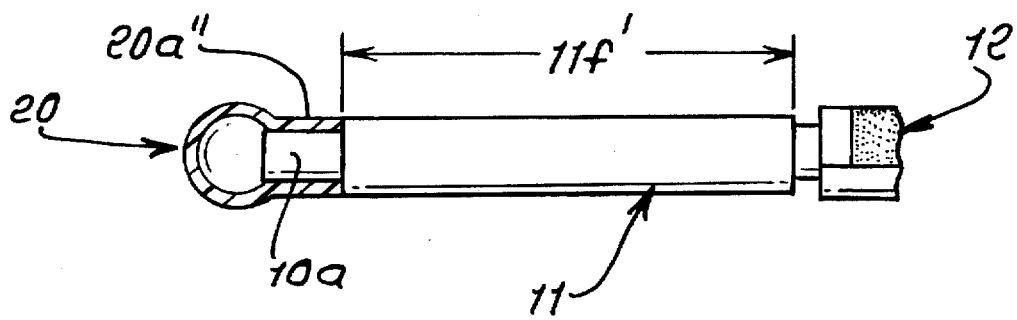
FIG. 9 is an elevation showing yet another modification.

In FIG. 9, the sleeve 20a" is also shortened and attached to the stick end portion 10a, and in endwise alignment with the strip 11. This also leaves the remaining length 11f' of the strip openly exposed for moisture contact.

Figure 10:
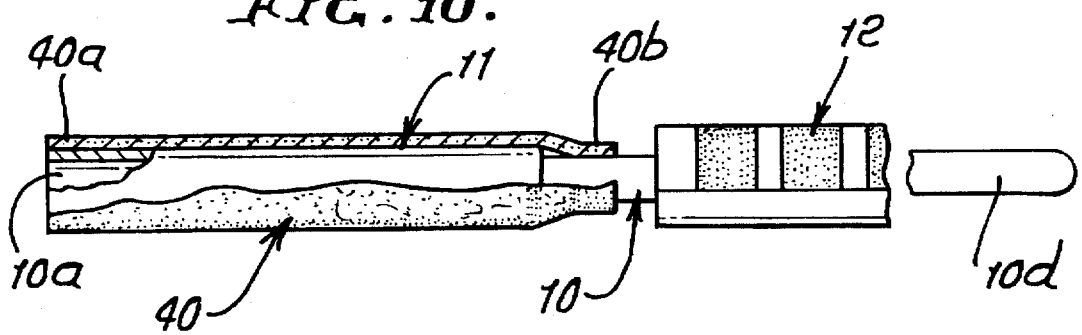
FIG. 10 is a view like FIG. 2, showing a protective porous layer applied over a pH indicator strip.

Referring now to the modification seen in FIG. 10, the elements the same as in FIG. 2 are given the same numerals. In addition a protective layer 40 in the form of a thin porous barrier, is applied adjacent the outer side of strip 11 so as to cover the latter (i.e. extend thereabout) and to be carried by the stick. Layer 40 allows vaginal moisture to penetrate through it and to contact the pH indicator strip 11, as during a test. Following the test, the strip 11 may be observed as described above, and for this purpose the layer 40 may be at least partly removed from adjacency to the strip, as by complete manual removal. Opposite end portions 40a and 40b of layer 40 may be initially attached as by light bonding or sticking to the ends of the strip 11, or to the stick, allowing pull-away removal of the layer at the end of the test. Such bonding agents are known, as on 3M Micropore Tape. Layer 40 acts as a barrier, during a test, to block direct contact of vaginal tissue with strip 11, preventing any possible irritation of such tissue.

Figure 11:
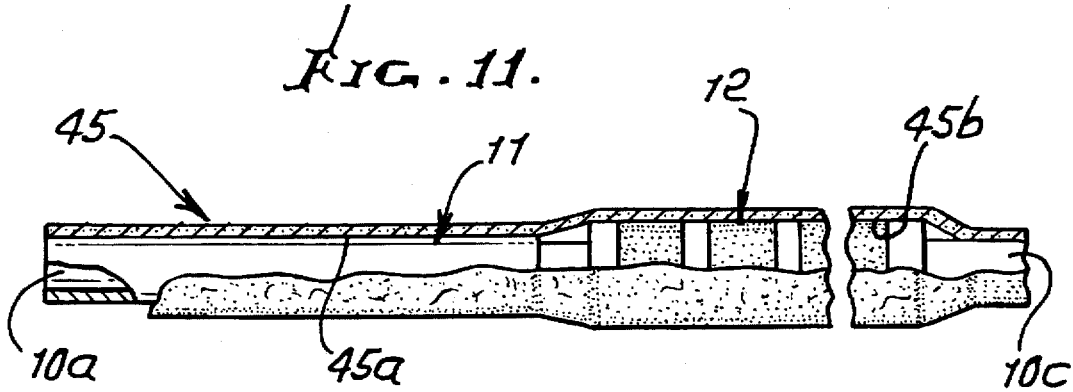
FIG. 11 is a view like FIG. 10, but showing the protective layer also applied over the color comparison measurement means.

In FIG. 11, the elongated layer 45 is like layer 40, but also extends over and about the color comparison measurement means 12, and is adhered, as described above, to the elements 11 and 12, as at 45a and 45b to completely cover 11 and 12 as during a test, while allowing pull-away of the layer 45 for visual observation of 11 and 12 after the test. Either one or both of 11 and 12 may be considered as a pH detecting means.

Figure 12:
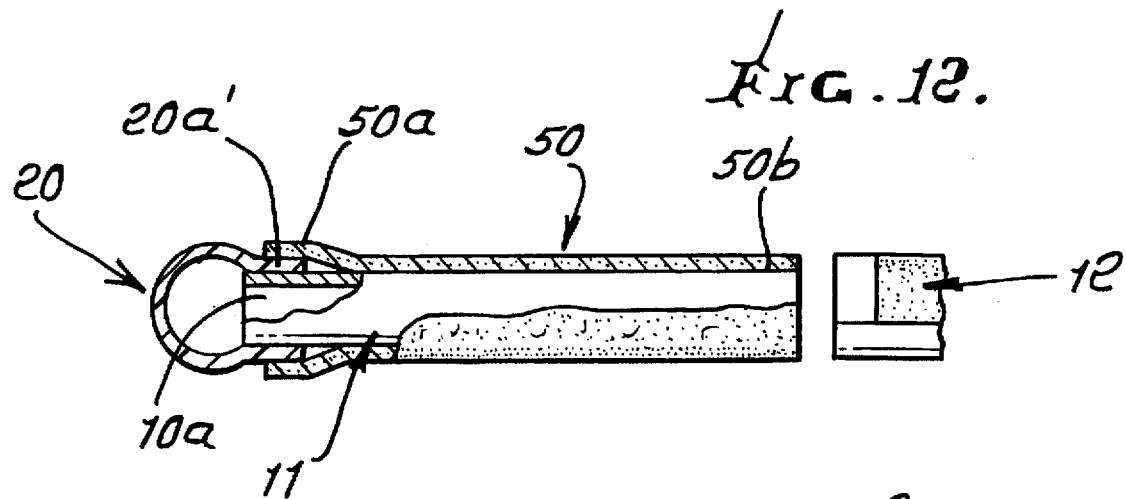
FIG. 12 is a view like FIG. 8, showing a protective porous layer applied over a pH indication strip.
Figure 12A:
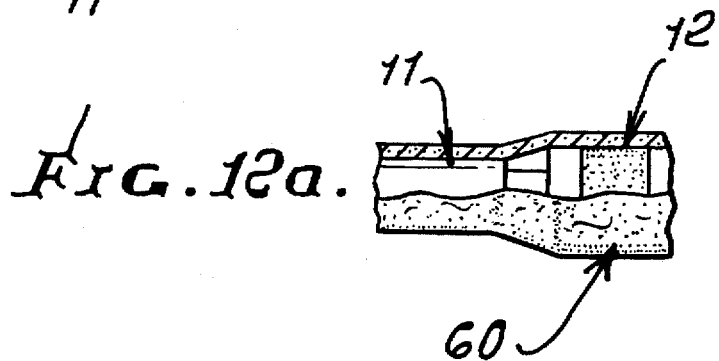
FIG. 12a is a view like FIG. 12, but showing the protective porous layer extending over the color comparison measurement means.

FIG. 12 is like FIG. 8, but layer 50 corresponding to layer 40 has its end 50a adhered to and about the sleeve 20a', while end portion 50b is adhered to the right end of strip 11, as shown. Note smooth surfaced blunt knob 20, as referred to above.

FIG. 13 is like FIG. 12, except that the layer 60, corresponding to 50, is elongated to cover the color comparison measurement means 12, and to adhere at 60b to the rightward end of 12.

In FIGS. 10-13, the porous barriers, as at 40, 45, 58 and 60 may consist of one or more barrier tissue layers, as for example are used in incontinence pads. One example is the outer layer of the Kimberly Clark product NEW DEPEND. Another usable barrier is the 3M product known as MICROPORE tape. One side of such tape is "tacky", i.e. weakly adhesive, so that it will adhere along the tape length to the elements 11 and/or 12 referred to. Barriers 45 and 50 as referred to may comprise such tape material.

In FIGS. 14-17, a modified elongated, narrow carrier stick 200 may consist of wood, plastic or other carrier material. A pH indication strip 201 such as phenaphthazine paper is adhered to one substantially flat side 200a of the stick 200, and near one end 200b, as by an adhesive. The strip 201 is elongated, and spaced from opposite edges 200c and 200d of the stick, as well as from end 200b. Typically, rectangular strip width is about 0.25 inches, and its length is about 1.5 inches. The stick width is about 0.375 inches, its length is about 5 inches and its thickness is about 0.125 inches.

The stick edges 200c and 200d are convexly curved or rounded as at 210 and 211 in FIG. 17. Also, the stick opposite ends 200f and 200g are convexly curved or rounded as at 212 and 213.

The handle portion 200e of the stick is desirably textured, as by provision of dimples 215 on side 200a of the stick. The length of such texturing may be about 1.5 inches, from end 200b. Such texturing aids finger and thumb gripping of the handle portion for accurate stick manipulation to position strip 201 adjacent the vaginal wall. Aiding of manipulation of the paper strip is enhanced by locating the texturing and paper strip at the same side of the stick. Note that the stick preferably has smooth top surface extent at 220 between 215 and 201, and also a smooth bottom surface at 221.

EXAMPLES

OBJECTIVES

To confirm the elevation of vaginal pH expected in patients with bacterial vaginosis and to examine the relationship of serum FSH and estradiol levels to vaginal pH in normal patients without vaginosis.

STUDY DESIGN 2,038 patients in a solo private practice underwent measurement of vaginal pH during routine pelvic examinations. 201 of these patients were chosen at random for this study. Measurements were made of serum levels of FSH and estradiol. Vaginal cultures were taken from 83 patients. Specimens were sent to a single commercial laboratory. Vaginal pH was determined by phenaphthazine (NITRAZINE®) pH paper. Vaginal pH was correlated with serum FSH, estradiol levels, and vaginal cultures using statistical analysis.

RESULTS

Vaginal pH was elevated in patients with documented vaginosis. Serum estradiol levels showed an inverse and serum FSH levels showed a direct statistical correlation with vaginal pH.

MATERIALS AND METHODS

Between May 1995 and May 1996, 2,038 patients in a private gynecologic practice were tested for vaginal pH. None of the patients were pregnant.

A total of 83 patients had vaginal cultures to study the effect of vaginosis on vaginal pH.

Two hundred one patients were tested for vaginal pH, serum FSH and serum estradiol. Of these 201 patients, 100 were on Estrogen Replacement Therapy and 8 were on oral contraceptives. Ninety-three patients were on no hormonal treatment. No patients tested were using vaginal medication.

Eighteen patients were tested for vaginal pH, serum FSH and serum estradiol on two separate occasions. Nine of these patients were tested before and after the use of estrogen. Nine patients were tested after a change in estrogen dose. In all nine cases, the estrogen does was increased. This separate study was done to observe the change in vaginal pH, serum FSH and serum estradiol in response to a change in estrogen therapy.

Phenaphthazine (NITRAZINE®) pH indicator paper was used for vaginal pH testing (NITRAZINE® pH indicator paper pH 4.5 to 7.5 range, distributed by APOTHECON®, a Bristol-Myers Squibb Company, Princeton, N.J.). This pH paper has been used for vaginal pH testing since 1938. The extended range of pH 4.5 to 7.5 proved to be easier to read and more comprehensive for vaginosis and vaginal estrogen level. Other pH testing papers were tried. (Hydrion® pH papers, Micro Essential Laboratory, 4224 Avenue H, Brooklyn, N.Y. 11210 (718) 338-3618). (ColorpHast® pH test strips, EM Science, 480 Democrat Road, Gibbstown, N.J. 08027 (800) 222-0342).

The pH paper was applied directly to the lateral vaginal wall at the outer third of the vagina. Care was taken to avoid cervical mucous (pH 7.0), blood (ph 7.4), or other substances (such as semen pH 7.0–8.0) and lubricating jelly known to affect vaginal pH. All samples were interpreted in incandescent light for accuracy.

All vaginal cultures were collected using the Star Swab, Starplex Transport System and were sent to Unilab Corporation, Tarzana, Calif., Venopuncture for blood samples was obtained within one hour of the vaginal pH test. Serum FSH was run on the Dade/Baxter, Inc. Stratus II automated instrument and reported as miU/mL. Female normal ranges are: Follicular Phase: 3.6–16.0 miU/ml, Mid Cycle Peak: 8.1–28.9 miU/ml, Luteal Phase: 1.8–11.7 miU/mL and Post Menopausal: 22.9–167.0 miU/mL. Serum estradiol was determined by radio immune assay, using Diagnostics Products Corporation's Coat A Count and reported as pg/mL. The normal range is 10–375. All tests were done at Huntington Memorial Hospital laboratory, Pasadena, Calif. Statistical analysis was performed by using the computer program "Statistical Package for Social Sciences" (SPSS).

Relationships between vaginal pH, serum estradiol and FSH levels were evaluated using Spearmans's Correlation Coefficients. Treated and untreated groups were compared for these variables using t-tests and ANOVA with Duncan Multiple Comparisons. Paired t-tests were used to compare the difference in means due to initiation or change of estrogen therapy.

RESULTS

Of 84 patients who had vaginal cultures, 27 grew normal flora, 14 yeast, 15 Beta-hemolytic-streptococcus, 14 gardnerella, and 13 mixed pathogens. The mean pH of three subgroups with bacterial vaginosis is significantly higher than that obtained in patients with either normal flora or yeast infection (One way ANOVA, p<0.05). There was no significant difference in the vaginal pH among the three subgroups with bacterial vaginosis, and there was no significant difference between the pH in patients with yeast infection and those with normal flora.

In the overall group of 201 women tested for vaginal pH, estradiol and FSH, vaginal pH correlated positively with serum FSH levels and negatively with serum estradiol using Spearman's correlation coefficients.

When the group of 201 women was divided into those on estradiol therapy and those on no treatment, significant differences were found between mean vaginal pH, serum estradiol levels, and serum FSH levels. These differences were significant despite the inclusion of some apparently normally cycling women in the untreated group. There was no significant difference in the mean age of the patients between the two groups.

The characteristics of 18 women studied both before and after initiation (n=9) or change (n=9) of estrogen replacement therapy showed that serum estradiol levels increased and FSH levels decreased significantly after initiation or changes of dose of ERT (p<0.003 and p<0.001 respectively, using paired t-testing). There was a significant decrease in vaginal pH from 6.1±0.7 to 4.6±0.3 (p<0.001) in the group who went from no treatment to estrogen replacement. Mean vaginal pH also decreased, although to a lesser degree of significance, in the women who went from lower dose to higher dose ERT (p=0.05).

The data obtained support the well documented body of literature indicating that vaginosis results in an elevated vaginal pH (5.0–6.5). For this reason alone, vaginal pH should become a routine test during most speculum examinations. Women should be encouraged to do vaginal pH testing to alert both pregnant and non-pregnant women to the possibility of sub-clinical vaginosis and to seek medical advice for proper diagnosis and treatment. The combination of pH testing, vaginal culture, and treatment as indicated, have shown a decrease in premature rupture of membranes and premature delivery.

The editorial comments of Watson A. Bowes, Jr. in the May 1996 issue of Obstetrical and Gynecological Survey are pertinent.

Statistically significant is the fact that the vaginal pH level, in the absence of vaginosis, is a reasonable marker for most patient's estradiol status. In addition, an elevated vaginal pH level in a well estrogenized patient is a reasonable marker for vaginosis. In this regard, detected pH correlates positively (directly) with FSH; and ph correlates negatively (inversely) with estradiol intake.

In consideration of all that as been said, vaginal testing for pH level appears to be that hoped for, reliable, "low-tech" tool. It certainly complies with the mandate for cost-effective, improved health care.

In the above, estrogen or estradiol can be administered orally, intermuscularly, or vaginally.

I claim:

1. In the method of determining need for estrogen replacement therapy or estrogen or estradiol dose change, the steps that include:

a) determining local acidity proximate a moist wall surface of the vagina, as differing from desired threshold level, and in the substantial absence of bacterial vaginosis, or vaginitis, b) and administering sufficient estrogen or estradiol or estrogenic substance to result in change in said acidity toward said level, c) said administering of sufficient estrogen or estradiol or estrogenic substance being effected on a periodic basis, and said determination of local acidity being repeated, whereby said local acidity is ultimately determined to have reached said desired level.

2. The method of claim 1 wherein said determining of local acidity includes employing an acidity indicator, and effecting contact of said indicator with said wall surface of the vagina.

3. The method of claim 2, wherein said indicator includes one of the following:

i) NITRAZINE® paper ii) phenaphthazine on a carrier iii) a material or materials exhibiting different colorations as a function of pH level.

4. The method of claim 1 wherein said threshold level is approximately 4.2 pH.

5. The method of claim 2 including providing a strip of material carrying said acidity indicator, and said determining of local acidity includes first contacting said strip with the wall surface of the vagina, and then observing said indicator on the strip.

6. The method of claim 5 wherein said indicator comprises a material or materials exhibiting colorations or other indications corresponding to pH levels of moisture of the wall surface of the vagina, said colorations being different for different pH levels.

7. The method of claim 2 including providing an elongated applicator on which said indicator is mounted, and manipulating said applicator to bring said indicator into said contact with the vaginal wall surface.

8. The method of claim 7 including providing said indicator in the form of a strip of material or materials mounted on an end portion of the applicator.

9. The method of claim 5 including manually manipulating said strip of material into contact with the wall surface of the vagina.

10. In the method of determining need for estrogen or estradiol or estrogenic substance change, in a human, the steps that include:

a) providing a pH detection means on a carrier stick, b) providing a protective porous layer adjacent said pH detection means, c) manipulating the stick to obtain pH detection of vaginal moisture, and including allowing vaginal moisture to penetrate said porous layer for contact with said pH detection means, d) visually observing said detection means, e) and determining from said observed pH detection means a need for a change in estrogen or estradiol or estrogenic substance level to be administered to a human female, f) said method carried out in the absence of bacterial vaginosis or vaginitis.

11. The method of claim 10 including, after said step c), removing said porous layer from adjacency to said pH detection means to allow said visually observing of said detection means.

12. The method of claim 10 including providing said pH detection means to include at least one of the following:

i) a pH indicating strip ii) a color comparison measurement means.

13. In the method of determining need for estrogen or estradiol or estrogenic substance change, the steps that include:

a) first determining local acidity proximate a moist wall surface of the vagina, said determining employed as an indicator of the presence or absence of bacterial vaginosis, b) and, after a vaginosis condition has been treated and eliminated, then again determining local acidity proximate a moist wall surface of the vagina, as differing from desired threshold level, c) and administering sufficient estrogen or estradiol or estrogenic substance to result in change in said acidity toward said threshold level.

14. The method of claim 13 wherein said administering of estrogen or estradiol or estrogenic substance is effected on a periodic basis.

15. The method of claim 13 wherein said administering of sufficient estrogen or estradiol is effected on a periodic basis, and in increasing or decreasing amounts, and said determination of local acidity is repeated, whereby said local acidity is ultimately determined to have reached said desired level.

16. The method of claim 13 wherein said determining of local acidity includes employing an acidity indicator, and effecting contact of said indicator with said wall surface of the vagina.

17. The method of claim 16 wherein said indicator includes one of the following:

i) NITRAZINE® paper ii) phenaphthazine on a carrier iii) a material or materials exhibiting different colorations or indications as a function of pH level.

18. The method of claim 13 wherein said threshold level is approximately 4.2 to 4.5 pH.

19. In the method of employing detected pH of vaginal moisture in estrogen therapy, the steps that include:

a) providing an acidity sensing means on a carrier, b) providing a protective porous layer adjacent said sensing means, c) manipulating the carrier proximate vaginal moisture, and including allowing vaginal moisture to penetrate said porous layer for contact with said sensing means, d) and detecting a vaginal moisture produced change in said sensing means, for determining need for a change in estrogen or estradiol or estrogenic substance dosage, e) and periodically administering sufficient estrogen or estradiol or estrogenic substance along with repeated detecting of vaginal moisture produced change in said sensing means to reduce said need to a desired level, said detecting taking place at intervals of up to about two weeks.

20. The method of claim 19 wherein said carrier is a stick, and including providing a smooth surfaced protective tip facing endwise at one end of the stick.

21. The method of claim 19 wherein said protective porous layer is provided to extend about a portion of said acidity sensing means.

22. The method of claim 19 wherein said carrier is a stick, and said protective porous layer is provided to extend about the stick, and over said acidity sensing means.

23. The method of claim 22 wherein said layer is provided in the form of a sleeve.

24. The method of claim 23 including providing a smooth surfaced protective tip facing endwise at one end of the stick, and in proximity to said sleeve.

* * * * *